United States Patent
Lee et al.

(10) Patent No.: US 8,143,035 B2
(45) Date of Patent: Mar. 27, 2012

(54) PANTOTHENATE KINASE OVEREXPRESSION AND PANTOTHENIC ACID SUPPLEMENTATION IN ACTINOMYCETES

(75) Inventors: Hei Chan Lee, Cheonan (KR); Jae Kyung Sohng, Asan (KR); Ka-Yiu San, Houston, TX (US)

(73) Assignee: Rice University, Houston, TX (US)

( * ) Notice: Subject to any disclaimer, the term of this patent is extended or adjusted under 35 U.S.C. 154(b) by 276 days.

(21) Appl. No.: 12/441,897

(22) PCT Filed: Sep. 22, 2006

(86) PCT No.: PCT/US2006/037107
§ 371 (c)(1),
(2), (4) Date: Mar. 18, 2009

(87) PCT Pub. No.: WO2008/039177
PCT Pub. Date: Apr. 3, 2008

(65) Prior Publication Data
US 2010/0047885 A1 Feb. 25, 2010

(51) Int. Cl.
*C12P 7/40* (2006.01)
*C12P 19/62* (2006.01)
*C07C 49/04* (2006.01)
(52) U.S. Cl. .................. 435/136; 568/382; 435/76
(58) Field of Classification Search .............. None
See application file for complete search history.

(56) References Cited

U.S. PATENT DOCUMENTS
4,766,071 A 8/1988 Simon et al.
2004/0199941 A1* 10/2004 San et al. .................. 800/281
2005/0089973 A1* 4/2005 Yocum et al. .............. 435/106

FOREIGN PATENT DOCUMENTS
WO PCT/US2006/037107 4/2008

OTHER PUBLICATIONS

Rude et al. (Engineered biosynthesis of polyketides in heterologous hosts, Chemical Engineering Science, vol. 59, pp. 4693-4701.*
Ruan et al., Acyltransferase Domain Substitutions in Erythromycin Polyketide Synthase Yield Novel Erythromycin Derivatives, Journal of Bacteriology, 1997, vol. 179, pp. 6416-6425.*
Salas et al., Genetic manipulation of antitumor-agent biosynthesis to produce novel drug, TIBTECH, 1998, vol. 16, pp. 475-482.*
Bate et al., The mycarose-biosynthesis genes of *Streptomyces fradiae*, producer of tylosin, Microbiology, 2000, vol. 146, pp. 139-146.*
Baltz et al., Molecular genetic methods for improving secondary-metabolite production in actinomycetes, Trends Biotechnol. 14(7):245-50 (1996).*
Nakashima et al., Actinomycetes as host cells for production of recombinant proteins, Microb Cell Fact. Mar. 23, 2005; 4:7; pp. 1-5.*

(Continued)

*Primary Examiner* — Alexander Kim
(74) *Attorney, Agent, or Firm* — Boulware & Valoir

(57) ABSTRACT

The invention relates to the synthesis of polyketides in *Actinomycetes* by overexpression of pantothenate kinase and supplementation with pantothenic acid. This results in increasing in vivo CoA production and thereby drives increased production of secondary metabolites, such as polyketides.

17 Claims, 7 Drawing Sheets

OTHER PUBLICATIONS

Alam, K.Y., et al., Anaerobic fermatation balance of *Escherichia coli* as observed by in vivo nuclear magnetic resonance spectroscopy. Journal of Bacteriology 171:6213-6217 (1989).

Blanco, et al., Identification of a sugar flexible glycosyltransferase from Streptomyces olivaceus, the producer of antitumor polyketide elloramycin. Chem Biol 8:253-263 (2001).

Hong, JS. et al., New olivosyl derivatives of methymycin/pikromycin from an engineered strain of *Streptomyces venezuelae*, FEMS Microbiol, Let., 2004, vol. 238:391.

Lampel, et al., Transformation and transfection of anthracycline-producing streptomycetes. Appl Environ Microbiol 51:126-131 (2001).

Lin H, Vadali RV, Bennett GN, San KY. Increasing the Acetyl-CoA Pool in the Presence of Overexpressed Phosphoenolpyruvate Carboxylase or Pyruvate Carboxylase Enhances Succinate Production in *Escherichia coli*. Biotechnol. Prog. (2004) 20(5):1599-604.

Mansi, El-Mansi et al., Control of Carbon Flux Through Enzymes of Central and Intermediary Metabolism During Growth of *Escherichia coli* on Acetate, Current Option in Microbiol. 2006, 9:173-179.

Mason A. B,et al., Alcohol Acetyltransferase and the Significance of Ester Synthesis in Yeast , Yeast, 2000, 16, 1287-1298.

Pfeifer, B.A. et al., Biosynthesis of Complex Polyketides in a Metabolically Engineered Strain of *E. coli*, 2001, Science 291: 1790-2.

Rock C.O. et al., Pantothenate Kinase Regulation of the Intracellular Concentration of Coenzyme A, J. Biol. Chem. 2000, 275, 1377-1383.

Russell, G.C. et al., Overproduction of the Pyruvate Dehydrogenase Multicomplex of *Escherichia coli* and Site-Directed Substitutions in the E1p and E2p Subunits, Biochem. J. 1992, 287:611-619.

San et al., Metabolic Engineering through Cofactor Manipulation and Its Effects on Metabolic Flux Redistribution in *Escherichia coli*, Metabolic Engineering 4:182-192 (2002).

Song, W. J. et al., Cloning, Sequencing, and Expression of the Pantothenate Kinase (coaA) Gene of *E. coli*, J. Bacteriol. 1992, 174:6411-6417.

Thuy, ML et al., Expression of 2-deoxy-scyllo-inosose synthase (kanA) from kanamycin gene cluster in *Streptomyces lividans*, 2005, Biotechnol. Lett. 27:465-70.

Vadali, R.V., Bennett GN, San KY. Cofactor Engineering of Intracellular CoA/acetyl-CoA and its Effect on Metabolic Flux Redistribution in *Escherichia coli*. Metab. Eng. (2004)6(2):133-9.

Vadali, R.V., Bennett GN, San KY. Enhanced Isoamyl Acetate Production Upon Manipulation of the Acetyl-CoA Node in *Escherichia coli*. Biotechnol Prog. (2004) 20(3):692-7.

Vadali, R.V.; Bennett, G. N.; San, K.-Y. Applicability of CoA/acetyl-CoA Manipulation System to Enhance Isoamyl Acetate Production in *Escherichia coli*. Metabolic Engineering. 2004a, 6, 294-299.

Vallari, D. et al., Biosynthesis and Degadation Both Contribute to the Regulation of Coenzyme A Content in *Escherichia coli*, J. Bacteriol. 1988, 170:3961-3966.

Voet, D. et al., Biochemistry, second edition, 1995, John Wiley & Sons, Inc., pp. 543-548.

Yang et al., Effect of Inactivation of nuo and ackA-pta on Redistribution of Metabolic Fluxes in *Escherichia coli*, Biotec. Bioeng. 1999, 65, 291-297.

Examples of ethyl esters, The Alchemist Web page printout, Mar. 18, 2008.

* cited by examiner

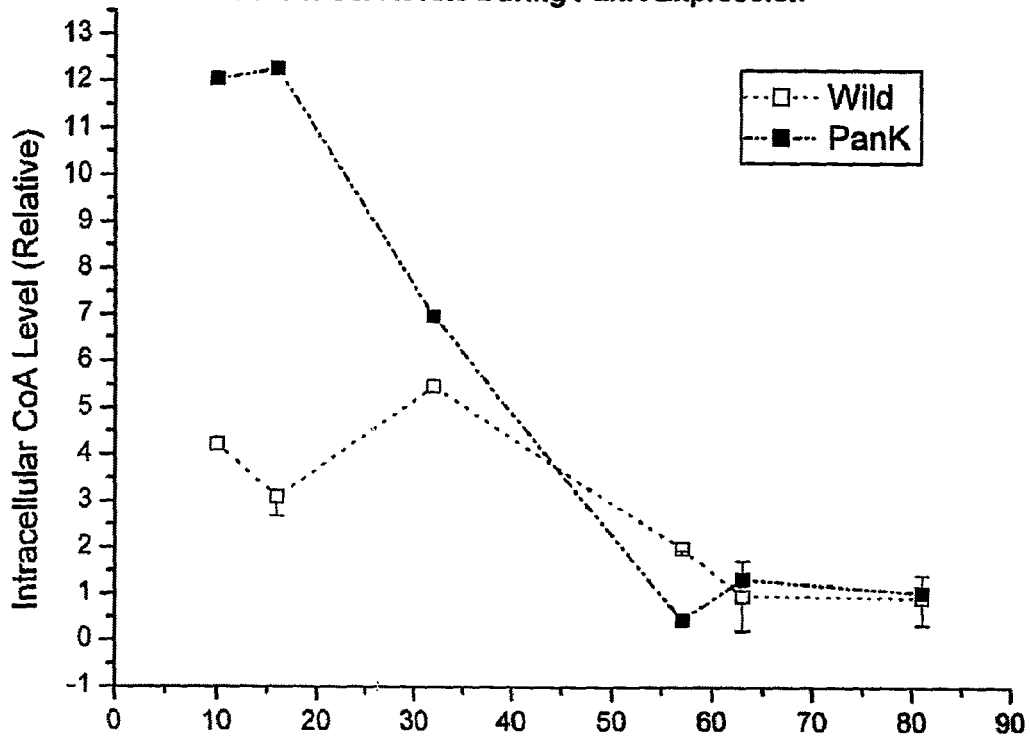
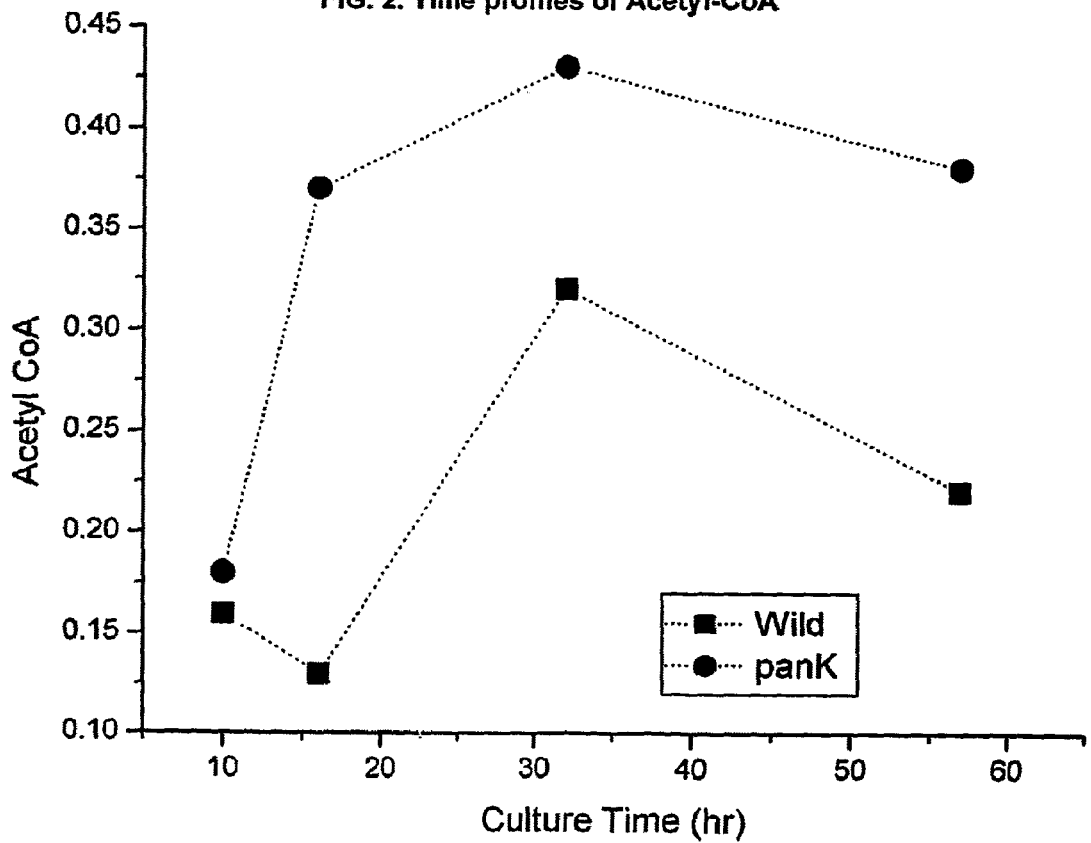

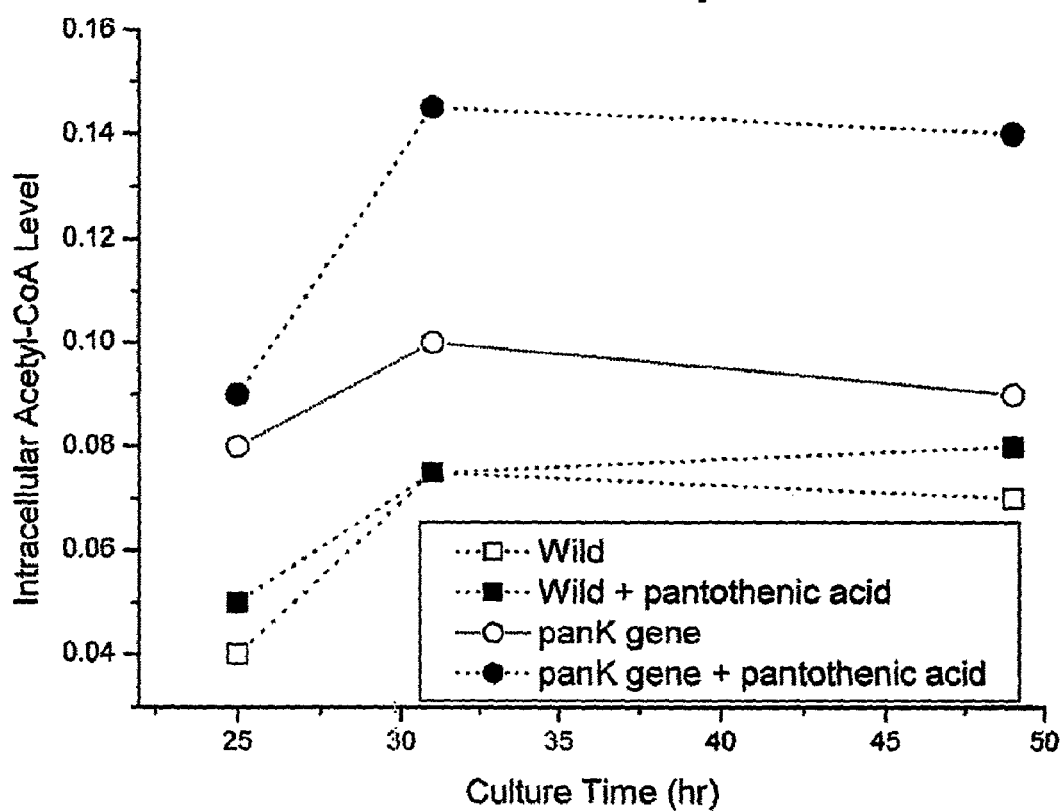

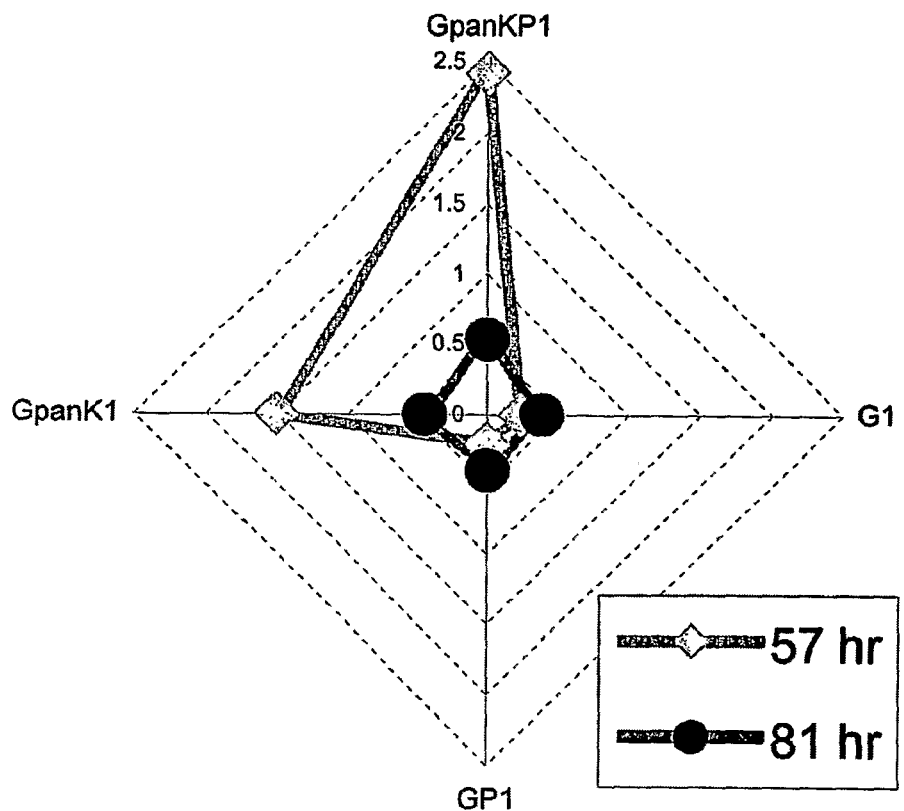
FIG. 4. Deoxyoleandolide production
G       : wild type,
GP1     : wild type + pantothenic acid supplementation
GPanK1  : pantothenate kinase overexpression
GPanKP1 : pantothenate kinase overexpression + pantothenic acid supplementation.
FIG. 5. Narnonolide production
Normalized Narnonolide Production
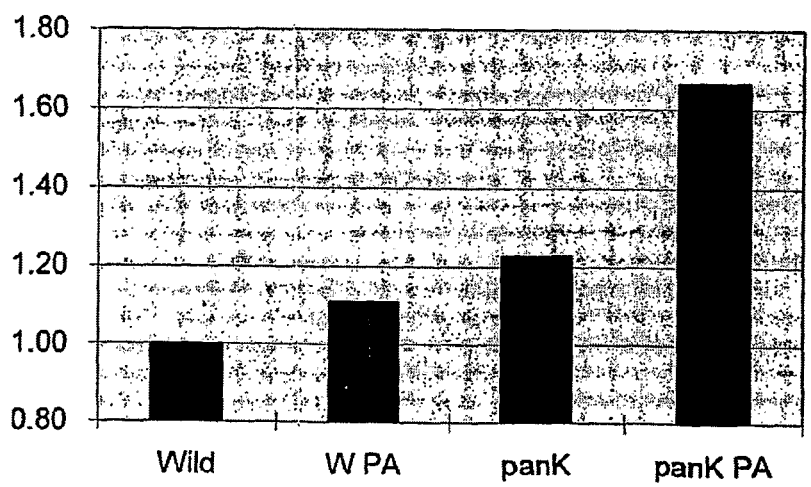

FIG. 6. Part of Polyketide Biosynthesis Pathway.
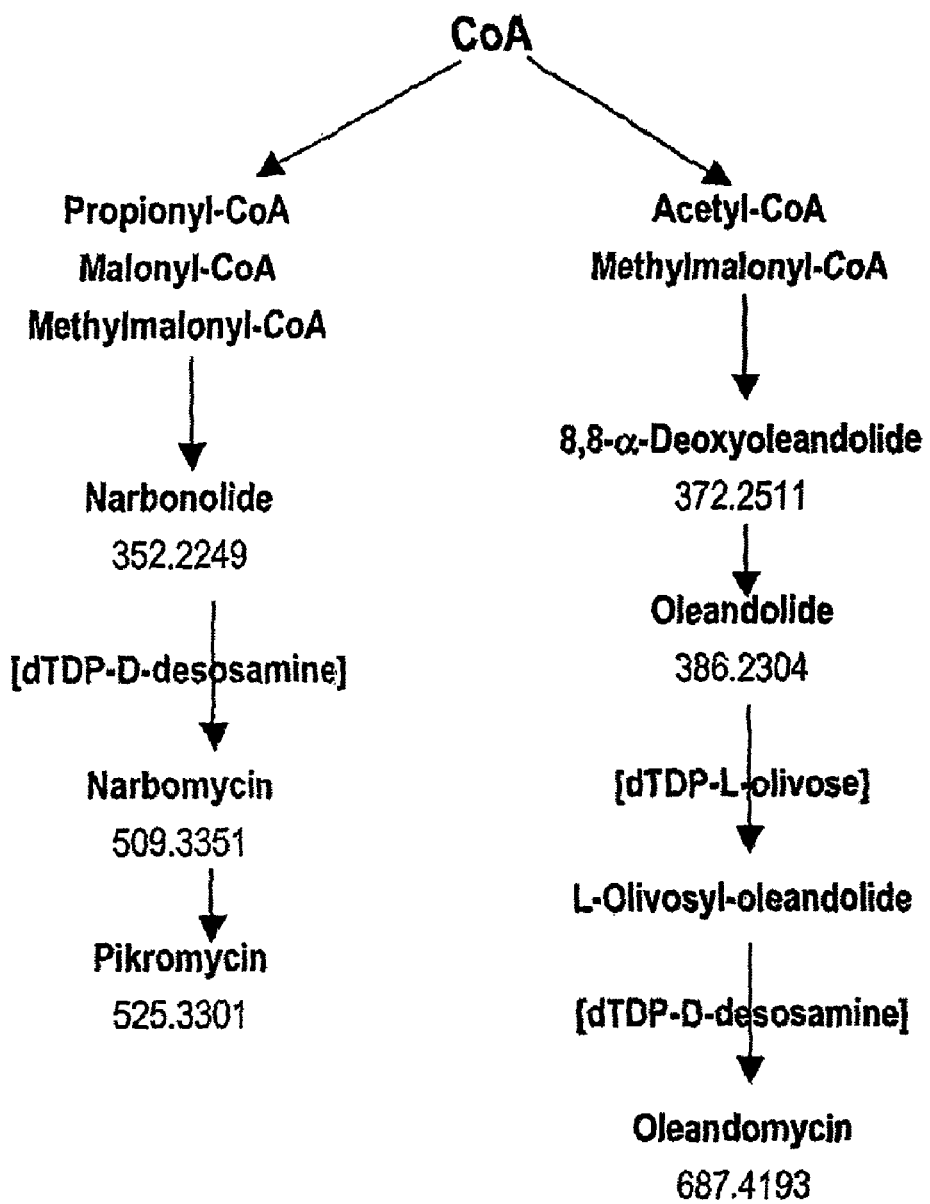

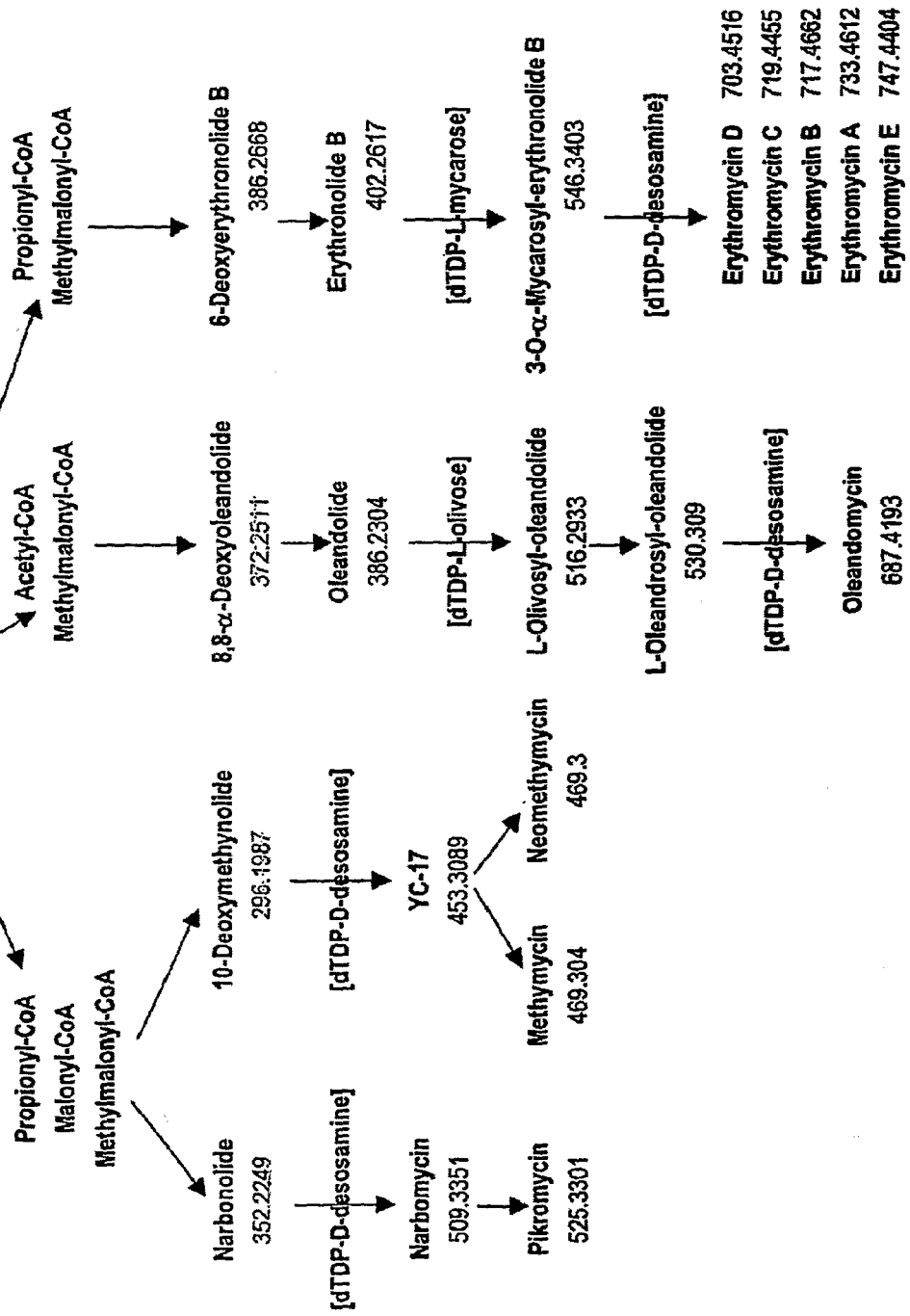
FIG. 7. Biosynthetic Pathway for Polyketides

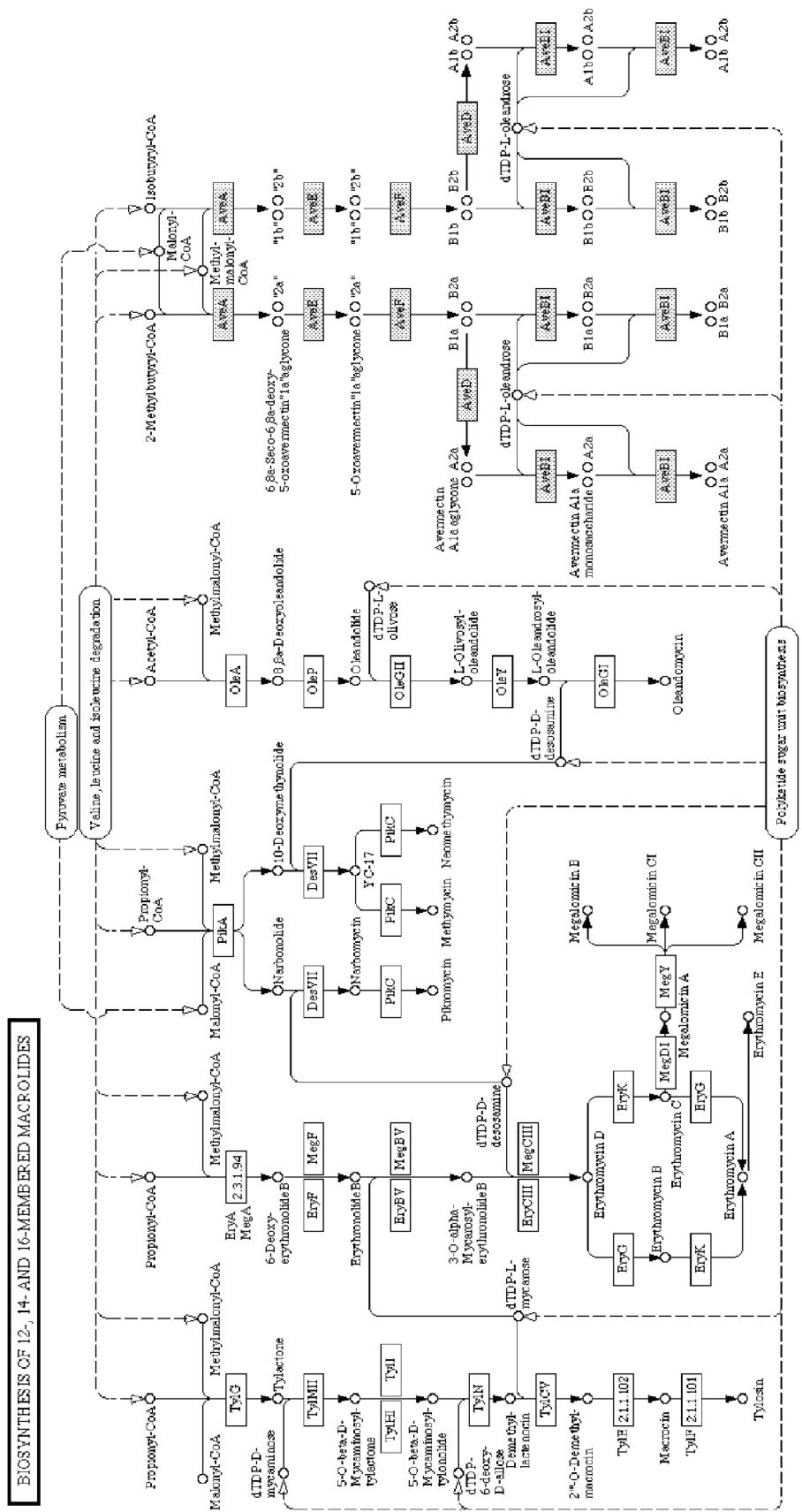
Figure 8a. Biosynthetic Pathways for Polyketides from KEGG

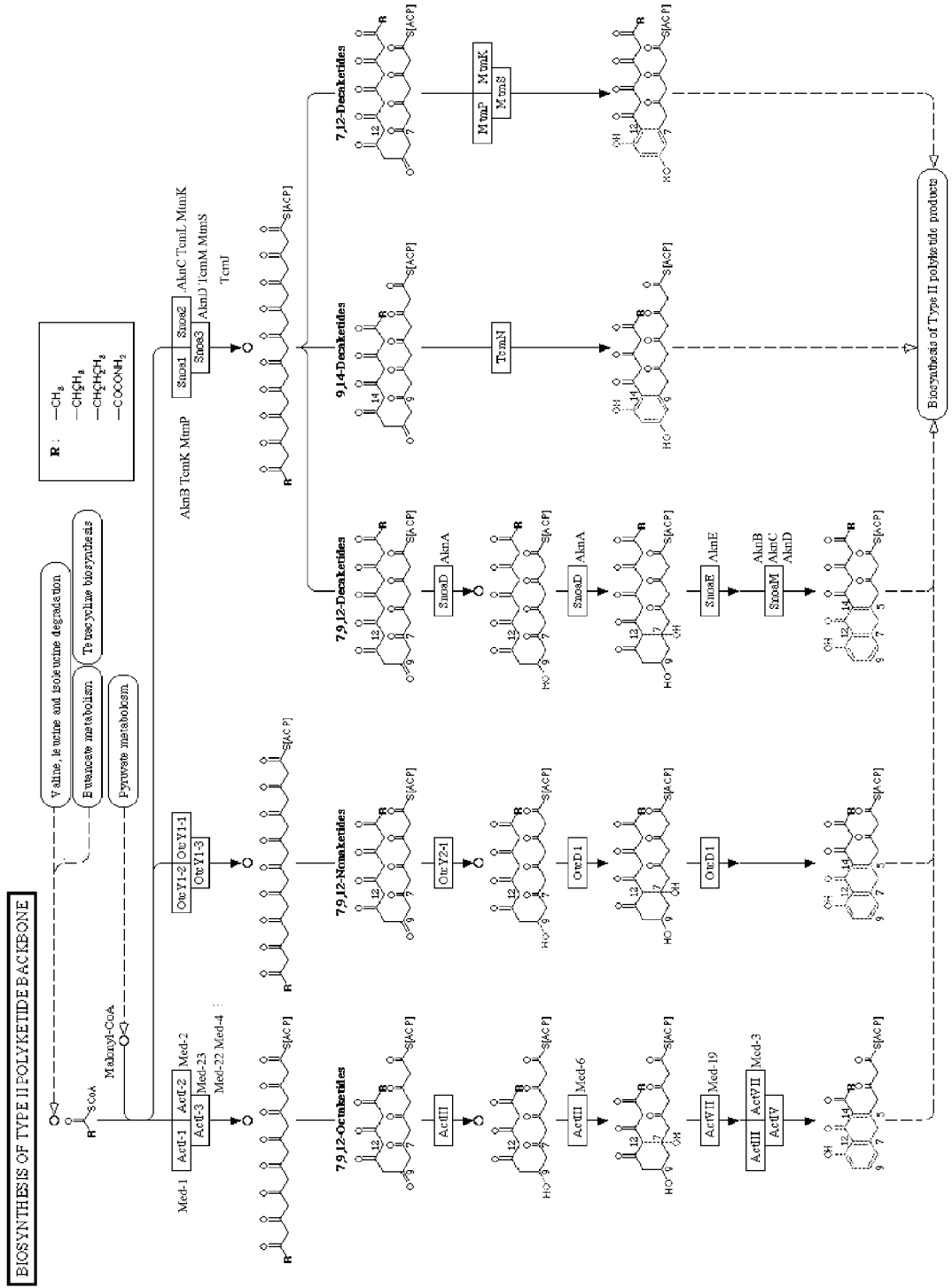
Figure 8b. Biosynthetic Pathways for Polyketides from KEGG

PANTOTHENATE KINASE OVEREXPRESSION AND PANTOTHENIC ACID SUPPLEMENTATION IN ACTINOMYCETES

CROSS-REFERENCE TO RELATED APPLICATIONS

This application is a 35 U.S.C. Section 371 of PCT/US2006/037107 filed Sep. 22, 2006, and incorporated herein by reference in its entirety.

FIELD OF THE INVENTION

The invention relates to the synthesis of polyketides in *Actinomycetes* by overexpression of pantothenate kinase (PanK) and supplementation with pantothenic acid, thus increasing in vivo CoA production and thereby also increasing the production of secondary metabolites, such as polyketides.

BACKGROUND OF THE INVENTION

The Actinobacteria or *Actinomycetes* are a phylum of Gram-positive bacteria. Most are found in the soil, playing an important role in decomposition of organic materials such as cellulose and chitin. Other Actinobacteria colonize plants and animals, and include a few pathogens such as *Mycobacterium*. Representative genera include: *Actinomyces, Arthrobacter, Bifidobacterium, Corynebacterium, Frankia, Micrococcus, Micromonospora, Mycobacterium, Nocardia, Propionibacterium*, and *Streptomyces*.

The actinobacteria are unsurpassed in their ability to produce compounds that have pharmaceutical activity. As early as 1940, Selman Waksman discovered that the soil bacteria he was studying made the antibiotic "actinomycin" and was awarded the Nobel Prize for his work. Since then hundreds of naturally occurring antibiotics have been discovered in these terrestrial microorganisms, especially from the genus *Streptomyces*. Therefore, this phylum is a very important source of medicinal compounds, and there is always a need to maximize the production of such pharmaceuticals.

One way of improving the production of any compound made by bacteria is through metabolic engineering—the purposeful re-design of an organism's metabolic pathways by recombinant DNA techniques. Metabolic engineering has the potential to considerably improve process productivity and is increasingly used in both academic and industrial institutions. Most current metabolic engineering studies have focused on manipulating enzyme levels. However, cofactors also play an essential role in a large number of biochemical reactions and their manipulation has the potential to be used as an additional tool to achieve desired metabolic engineering goals.

For example, Coenzyme A (CoA) is an essential cofactor in numerous reactions and is involved in the regulation of key metabolic enzymes. In fact, it has been estimated that as much as 4% of all enzymes utilize CoA, CoA thioesters, or 4'-phosphopantetheine as substrates. Further, CoA compounds, including acetyl-CoA, propionyl-CoA, malonyl-CoA, and methylmalonyl-CoA, are essential precursors required for the biosynthesis of polyketides and other complex biomolecules.

Polyketides are small, cyclized molecules. Between 5000 and 10,000 are known, and about 1% of them possess drug activity. Sales of the more than 40 polyketide drugs—including antibiotics, immunosuppressants, cholesterol-lowering agents, antifungals, and cancer chemotherapeutics—exceed $15 billion a year. But polyketides are difficult to synthesize chemically, and the exotic microbes that produce them naturally can be hard to grow in culture.

Sugars are the structural components of different types of natural products. Important antibiotics, antifungals, antiparasites and anticancer drugs possess sugars attached to the aglycon core. These sugar components participate in the molecular recognition of the cellular target by the bioactive compound and, therefore, its presence is important, in many cases essential, for the biological activity of many natural products. A great majority of these sugars belong to the 6-deoxyhexoses (6DOHs). These sugars are synthesized from nucleoside diphosphate-activated hexoses (mainly D-glucose) via a 4-keto-6-deoxy intermediate. Two common enzymatic steps leading to the biosynthesis of this intermediate are catalyzed by a dNDP-D-hexose synthase and dNDPD-hexose-4,6-dehydratase. The different 6DOHs will vary depending on the substituents and/or the stereochemistry at carbon atoms at positions 2, 3, 4, or 5 of the hexose carbon chain, resulting from deoxygenations, transaminations and/or C, N, or O methylations. D- and L-isomeric forms of many 6DOHs exist as a result of the action of a 5- or a 3,5-epimerase.

In recent years, a number of 6DOHs gene clusters have increasingly been characterized, most of them participating in the biosynthesis of different antibiotics produced by *Actinomycetes*. Deoxy sugar carrying glycosides and polysaccharides are believed to be secondary gene products, which are synthesized from activated sugars by glycosyltransferases. The activation is brought about in analogy to mammalian pathways by nucleoside diphosphates. It is the activated sugar that is derivatized in general before being transferred to the respective aglycon. The deoxysugars are transferred to the corresponding aglycon by glycosyltransferases, which are generally sugar-, aglycon-, and site-specific. In recent years, increasing evidence has suggested some degree of "flexibility" of glycosyltransferases involved in the biosynthesis of secondary metabolites, and there have been some reports of examples in which different deoxysugars have been transferred by a glycosyltransferase to its aglycon. One of these glycosyltransferases, the elloramycin glycosyltransferase (ElmGT), has been shown to be especially "flexible" in accepting different L- and D-deoxysugars and also being able to transfer a disaccharide. Recently, several plasmids that direct the biosynthesis of L-daunosamine, L-Olivose, L-oleandrose or D-desosamine have been reported by the different groups. These plasmids contain different subsets of genes involved in the biosynthesis of these deoxysugars from several antibiotic-producing organisms.

What is needed in the art are metabolic engineering methods that can be applied to *Actinomyces*, such as *Streptomyces*, to increase the production of polyketides and other complex biomolecules.

*E. coli* have been already been metabolically engineered to increase CoA production (4), whereby a 10 fold increase in CoA and a 5 fold increase in acetyl-CoA was seen on overexpression of the panK gene and supplementation with pantothenic acid. However, the metabolic engineering of *E. coli* is not easily applied to the *Actinomycetes*, which is a much more difficult bacterial phylum to engineer (2). Further, early attempts were only made to improve the production of primary CoA products and acetyl-coA, and improved production of secondary metabolites was not attempted.

SUMMARY OF THE INVENTION

The invention generally relates to the metabolic engineering of *Actinomycetes*. By using the panK gene with pantothenic acid as a supplement to promote the biosynthesis of CoA in polyketide producing *Actinomycetes*, the levels of secondary metabolites such as polyketides production are increased. Other compounds, including amino acids, can also be optimized in the media composition to further improve yield.

TABLE 1

ABBREVIATIONS

| Abbr | Term |
|---|---|
| 3PG | 3-phosphoglycerate |
| A-CoA | Acetyl-Coenzyme A |
| AKG | α-ketoglutarate |
| Ap | ampicillin |
| Ap$^R$ | ampicillin resistance |
| ATCC ® | American Tissue-type Culture Collection |
| Cm | chloramphenicol |
| Cn | carbenicillin |
| CoA | Coenzyme A |
| ColE1 | gram-negative origin of replication |
| DesVII | glycosyl transferase |
| DesVIII | |
| DOH | deoxyhexoses |
| ElmGT | elloramycin glycosyltransferase |
| Em | erythromycin |
| GC-MS | gas chromatography-mass spectroscopy |
| KEGG | Kyoto Encyclopedia of Genes and Genomes |
| Km/Km$^R$ | kanamycin or kanamycin resistance |
| MLS$^R$ | macrolide, lincosamide and streptogramin A resistance |
| Nal | nalidixic acid |
| NCBI ™ | National Center for Biotechnology Information |
| OAA | oxaloacetate |
| OriII | Gram-positive origin of replication |
| Ox | oxacillin |
| PanK | pantothenate kinase |
| PS | pantothenate synthetase |
| $R$ | Superscript R indicates antibiotic resistance |
| Sm/Sm$^R$ | streptomycin or streptomycin resistance |
| SPA medium | Sporulation medium, see recipe below |
| Tc | tetracycline |
| Thi$^R$/Cm$^R$ | thiamphenicol/chloramphenicol resistance |
| wt | wild-type |

Polyketide production in an *Actinomycetes* cell is increased by producing an engineered *Actinomycete* that overexpresses a pantothenate kinase (panK) gene, and growing the cell in a medium supplemented with pantothenic acid, this causes the bacteria to produce more polyketide than a wild type *Actinomycete* grown in said medium not supplemented with pantothenic acid.

An engineered *Actinomycetes* cell comprising a recombinant pantothenate kinase (panK) gene is also described. The engineered *Actinomycetes* increases PanK activity and polyketides synthesis.

Polyketide production is increased in an *Actinomycetes* bacteria by transforming an *Actinomycete* with a vector that encodes a pantothenate kinase (panK) gene, and growing the bacteria under conditions that allow overexpression of said panK gene and in a medium supplemented with pantothenic acid. These engineered *Actinomycetes* produce more polyketides than wild-type *Actinomycetes* grown without pantothenic acid.

The *Actinomycete* can be a *Streptomyces*, more specifically *Streptomyces venezuelae* or *Streptomyces peucetius*.

The addition of recombinant DNA encoding a sugar transferase, glycosyltransferase, sugar synthase, glycosylsynthase, and/or sugar dehydratase directs polyketides synthesis of different products. The DesVII, DesVIII, elloramycin glycosyltransferase (ElmGT), and dNDP-D-hexose synthase dNDPD-hexose-4,6-dehydratase are some examples of sugar modifying enzymes that may be used in the present invention The panK gene is expressed from a chromosomal integration, phage, plasmid, or shuttle vector comprising the panK gene operably linked to a promoter. The panK gene encodes a protein that phosporylates panthenoic acid to phosphopantetheine, more specifically the PanK protein is selected from table 2, one example being the *E. coli* panK gene.

CoA concentration is increased 2 fold in cells with PanK than cells without the PanK gene.

BRIEF DESCRIPTION OF THE DRAWINGS

FIG. 1: Effect of PanK overexpression on intracellular CoA level.
FIG. 2: Time profiles of A-CoA concentration in *S. venezuelae* with and without PanK overexpression.
FIG. 3: Effects of PanK overexpression and pantothenic acid supplementation on the intracellular A-CoA level.
FIG. 4: Deoxyoleandolide production in *S. venezuelae*.
FIG. 5: Narbonolide production in *S. venezuelae*.
FIG. 6: Polyketide biosynthesis pathway.
FIG. 7: Biosynthetic pathway for polyketides.
FIG. 8: Detailed biosynthetic pathway for polyketides from KEGG.

DESCRIPTION OF EMBODIMENTS OF THE INVENTION

As used herein "polyketide" is defined as a large class of diverse compounds that are characterized by more than two carbonyl groups connected by single intervening carbon atoms, and also include derivatives of same, such as glycosylated polyketides. Polyketides include various substances having antibiotic, anticancer, cholesterol-lowering, and/or immunosuppressive effects.

Some examples of polyketides include: amphotericin B; antimycin A; brefeldin A; candicidin; epothilones; erythromycin; azithromycin; clarithromycin; erythromycin estolate; erythromycin ethylsuccinate; roxithromycin; ivermectin; josamycin; ketolides; leucomycins; kitasamycin; spiramycin; lovastatin; lucensomycin; macrolides; maytansine; mepartricin; miocamycin; natamycin; nystatin; oleandomycin; troleandomycin; oligomycins; rutamycin; sirolimus; tacrolimus; tylosin; oleandomycin; deoxyoleandolide; narbonolide; narbomycin and pikromycin.

Chiral compounds can include diasteriomers, entantiomers and mixtures (R-trans, R-cis, S-trans, and S-cis) unless a single chiral compound is specifically identified as the desired product. Biological reactions can produce a variety of compounds, diasteriomers, entantiomers and mixtures (R-trans, R-cis, S-trans, and S-cis) unless the reaction product is specifically identified as a single compound.

"Deoxy sugars" include deoxyhexose, 2-deoxyhexose, 6-deoxyhexose, rhamnose, fucose, and deoxyribose that are precursors to many biomolecules.

The terms "operably associated" or "operably linked," as used herein, refer to functionally coupled nucleic acid sequences.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, and the like. By "null mutant" or "null mutation" what is meant is that activity is completely inactivated. In one example, the control plasmid is inserted without the gene of interest. In another example the gene of interest is completely removed by recombination. Additionally, the gene of interest may be removed by inactivation, mutation, or truncation which eliminates activity.

"Overexpression" or "overexpressed" is defined herein to be at least 150% of protein activity as compared with an appropriate control species. Preferably, the activity is increased 100-500%. Overexpression is achieved by mutating the protein to produce a more active form or a form that is resistant to inhibition, by removing inhibitors, or adding activators, and the like. Overexpression can also be achieved by removing repressors, adding multiple copies of a gene to the cell, up-regulating an existing gene, adding an exogenous gene, and the like.

The terms "disruption" and "disruption strains," as used herein, refer to cell strains in which the native gene or promoter is mutated, deleted, interrupted, or down regulated in such a way as to decrease the activity of the gene. A gene is completely (100%) reduced by knockout or removal of the entire genomic DNA sequence. Use of a frame shift mutation, early stop codon, point mutations of critical residues, or deletions or insertions, and the like, can completely inactivate (100%) gene product by completely preventing transcription and/or translation of active protein.

The term "exogenous" indicates that the protein or nucleic acid is introduced from outside the organism or system, without regard to species of origin. For example, an exogenous peptide may be applied to the cell culture, an exogenous RNA may be expressed from a recombinant DNA transfected into a cell, or a native gene may be under the control of exogenous regulatory sequences or duplicated to increase expression.

As used herein "recombinant" is relating to, derived from, or containing genetically engineered material. Recombinant DNA can be carried on a vector or integrated into the chromosome of the host bacteria. Many vectors are known which can be used in a variety of species. Stable chromosomal integration methods are also well documented. In one method, recombinant DNA is integrated using P1 phage transduction and one-step inactivation based on λ red recombinase (Datsenko and Wanner, 2000). Briefly, a gene of interest is cloned adjacent to a selectable marker, both of which are flanked by chromosomal DNA sequence. When the recombinant DNA is inserted into a cell, the recombinant DNA integrates into the chromosome. Stably integrated DNAs are selected by serial plating on the selectable marker. Often the selectable marker is removed by recombination leaving the stable recombinant DNA in the host cell.

A gene or cDNA may be "optimized" for expression in *E. coli*, or other bacterial species using the codon bias for the species. Various nucleotides can encode a single peptide sequence. Understanding the inherent degeneracy of the genetic code allows one of ordinary skill in the art to design multiple nucleotides which encode the same amino acid sequence. NCBI™ provides codon usage databases for optimizing DNA sequences for protein expression in various species.

"Pantothenate kinase" or "PanK" can be the *E. coli* panK gene or PanK protein sequence, or the panK gene can be from other species either wild-type or optimized for expression in *Actinomycetes*. There are over 650 PanK proteins available in the GenBank™ database. Non-limiting examples of PanK proteins are listed in Table 2.

TABLE 2

PANK PROTEINS FROM VARIOUS SPECIES

| Acc # | Protein | % ID *E. coli* | % ID Human |
|---|---|---|---|
| NP_418405 | *E. coli* K12 PanK | 316/316 (100%) | — |
| YP_405196 | *Shigella dysenteriae* Sd197 PanK | 315/316 (99.7%) | — |
| YP_410267 | *Shigella boydii* Sb227 PanK | 315/316 (99.7%) | — |
| NP_290609 | *E. coli* O157:H7 PanK | 308/308 (100%) | — |
| NP_709774 | *Shigella flexneri* 2a str. 301 PanK | 307/308 (99.7%) | — |
| NP_838910 | *Shigella flexneri* 2a str. 2457T PanK | 307/308 (99.7%) | — |
| NP_463013 | *Salmonella typhimurium* LT2 PanK | 302/316 (95.6%) | — |
| NP_457926 | *Salmonella enterica* PanK | 302/316 (95.6%) | — |
| ZP_00733622 | *E. coli* 53638 PanK | 304/304 (100%) | — |
| NP_407208 | *Yersinia pestis* PanK | 271/316 (85.8%) | — |
| ZP_00831732 | *Yersinia intermedia* ATCC 29909 PanK | 268/316 (84.8%) | — |
| ZP_00827575 | *Yersinia frederiksenii* ATCC 33641 PanK | 269/316 (85.1%) | — |
| YP_048342 | *Erwinia carotovora* PanK | 263/316 (83.2%) | — |
| NP_931893 | *Photorhabdus luminescens* PanK | 249/316 (78.8%) | — |
| NP_872682 | *Haemophilus ducreyi* PanK | 203/316 (64.2%) | — |
| NP_229974 | *Vibrio cholerae* PanK | 200/311 (64.3%) | — |
| YP_089380 | *Mannheimia succiniciproducens* PanK | 202/320 (63.1%) | — |
| ZP_00732116 | *Actinobacillus succinogenes* PanK | 193/315 (61.3%) | — |
| YP_630545 | *Myxococcus xanthus* PanK | 174/305 (57.1%) | — |
| ZP_00713767 | *E. coli* B7A PanK | 166/166 (100%) | — |
| YP_641294 | *Mycobacterium* PanK | 167/311 (53.7%) | — |
| NP_353076 | *Agrobacterium tumefaciens* PanK | 163/312 (52.2%) | — |
| NP_390257 | *Bacillus subtilis* PanK | 158/318 (49.7%) | — |
| ZP_00708599 | *E. coli* B171 PanK | 133/134 (99.3%) | — |
| YP_139293 | *Streptococcus thermophilus* PanK | 128/312 (41.0%) | — |
| XP_215283 | *Rattus norvegicus* PanK1 | — | 472/558 (84%) |
| XP_215826 | *Rattus norvegicus* PanK2 | — | — |
| XP_340786 | *Rattus norvegicus* PanK3 | — | 287/359 (79%) |
| NP_076281 | *Mus musculus* PanK1 β | — | 360/374 (96%) |
| NP_705721 | *Mus musculus* PanK2 | — | 302/372 (81%) |
| NP_683878 | *Homo sapiens* PanK1.α | — | 598/598 (100%) |
| NP_683879 | *Homo sapiens* PanK1.β | — | 365/374 (97%) |
| NP_612189 | *Homo sapiens* PanK1.γ | — | 363/363 (100%) |
| NP_705902 | *Homo sapiens* PanK2.1 preproprotein | — | 305/372 (81%) |
| NP_079236 | *Homo sapiens* PanK2.2 | — | 227/278 (81%) |

TABLE 2-continued

PANK PROTEINS FROM VARIOUS SPECIES

| Acc # | Protein | % ID E. coli | % ID Human |
|---|---|---|---|
| NP_078870 | Homo sapiens PanK3 | — | 290/359 (80%) |
| NP_060686 | Homo sapiens PanK4 | — | 128/354 (36%) |

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 11 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W word size [Integer] default=11 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs.

This program is available online at NCBI™ (ncbi.nlm.nih.gov/BLAST/).

Common restriction enzymes and restriction sites are found at NEB® (New England Biolabs®, neb.com) and Invitrogen® (invitrogen.com). ATCC®, American Type Culture Collection™ (atcc.org), DSMZ®, Deutsche Sammlung von Mikroorganismen and Zellkulturen™ (dsmz.de). KBIF®, Korean Biological Resource Center™ (kbif.kribb.re.kr), and WDCM®, World Data Centre for Microorganisms™ (wdcm.nig.acjp) have extensive collections of cell strains that are publicly available. NEB®, Invitrogen®, ATCC®, DSMZ®, KBIF®, and WDCM® databases are incorporated herein by reference.

Plasmids and strains used in certain embodiments of the invention are set forth in Table 3.

TABLE 3

PLASMIDS AND STRAINS

| Plasmid/Strain | Genotype | Ref |
|---|---|---|
| pIBR25 | E. coli-Streptomyces shuttle vector | 3 |
| pIBR25-PanK | pIBR25 with panK gene from E. coli, see NP_418405 | herein |
| Streptomyces venezuelae | wild-type | ATCC 10712 |
| Δ desosamine | Streptomyces venezuelae Δdesosamine cluster | 1 |

Streptomyces venezuelae or S. venezuelae was originally isolated in 1948. Bacteria with similar genetic backgrounds are available through a variety of sources including ATCC® 10712, ATCC® 25508, CBS 650.69, DSM 41109, DSMZ® 40230, DSMZ® 40612, DSMZ® 40634, DSMZ® 40727, DSMZ® 41110, DSMZ® 41111, IFO 12595, IFO 13096, IMET 41356, IMRU 3534, IMRU 3625, ISP 5230, JCM 4526, KCC S-0526, NBRC 12595, NBRC 13096, NRRL B-2277, RIA 1288, VKM Ac-589, and other S. venezuelae strains available through different sources. All of these strains are expected to function in the experiments described given the similar genetic background.

"Shuttle vector" is a vector with two or more origins of replication for different species. This allows the vector to replicate in more than one species. The pIBR25 vector has an E. coli and S. venezuelae origin of replication. The E. coli origin allows high levels of plasmid replication in E. coli for cloning and genetic manipulation. The S. venezuelae origin allows expression of proteins in Streptomyces. Over 200 shuttle vectors are available through ATCC® alone. A shuttle vector can be generated for any species by cloning an origin of replication into a plasmid that already contains an origin for another species.

When plasmids are used, the effect of host/plasmid interaction is minimized by comparing three different systems consisting of: the host only, a plasmid expressing biologically active enzyme, and a control system with the expression vector alone.

EXAMPLE 1:

Materials and Methods

E. coli was grown in Luria-Bertani broth (LB) with pH of 7.5 containing kanamycin and ampicillin. Cells were innoculated at $5 \times 10^5$ cells/ml and grown in a shaker flask, with rotation at 150 rpm, for 12 hours.

S. venezuelae cells were cultured in SPA medium containing per liter 1 gram of yeast extract, 1 gram of beef extract, 2 gram of tryptose, 10 gram of glucose, trace amount of ferrous sulfate, and appropriate antibiotics (25 μg/mL of thiostrepton or 50 μg/mL of kanamycin). Cells were innoculated at $5 \times 10^5$ cells/ml and grown in a shaker flask, with rotation at 150 rpm, for sampling. CoA and acetyl-CoA were assayed by HPLC according to the method described in Metabolic Engineering 6:133-139(2004). Metabolites were assayed by LC-MS system equipped with a reverse phase column (XTerra MS C18, Waters Co., MA) with the electrospray source with photodiode array detector. 10 mM ammonium acetate buffer solution was used as the mobile phase at a flow rate of 0.2 ml/min. The column was operated at 30° C.

EXAMPLE 2:

Pank Overexpression

S. venezuelae cells (wild type) were transformed by protoplast fusion using the E. coli-Streptomyces shuttle vector pIBR25 containing the panK gene from E. coli (pIBR25-PanK), added to the vector at the BamHI restriction sites. The transformed Streptomyces cells were unstable until the cloned gene was integrated into the chromosome. To select the stable transformants, several generations of transfer to the fresh media with selection pressure was performed. The transformed cells were then grown in pantothenic acid supplemeted medium (1 mg/ml), and CoA and acetyl-CoA levels were measured.

The data in FIG. 1 shows that overexpression of one of the upstream rate-controlling PanK together with pantothenic acid supplementation enhances the intracellular concentration of coenzyme A compounds. Initial intracellular CoA levels were about three times higher than that of wild type strain.

Similarly, FIG. 2 demonstrates that intracellular acetyl-CoA level was higher (about 30% higher) throughout the culture period with panK gene and the supplementation of pantothenic acid in the *Streptomyces* culture. Final acetyl-coA concentration was also about 2 fold higher in the engineered bacteria as compared with wild type.

We then studied the separate effects of PanK overexpression from the effects of pantothenic acid supplementation by employing the appropriate controls. FIG. 3 clearly separates those two effects and even shows synergistic effects of PanK overexpression and pantothenic acid supplementation on the intracellular acetyl-CoA level.

EXAMPLE 3:

Secondary Metabolite Production

Improving CoA and/or acetyl-CoA levels is a good first step, but it is also necessary to translate these gains into increased production of the desired secondary metabolite. To demonstrate that this goal was achievable, we stimulated deoxyoleandolide production in *S. venezuelae*. Cells were transformed with pIBR25-PanK or pIBR25. Stable transformants were selected by serial culture, as previously described.

One of the polyketides in the oleandomycin biosynthesis pathway (see FIG. 6) called 8,8-α-deoxyoleandolide was much higher for *S. venezuelae* with PanK overexpression and pantothenic acid supplementation (see grey circles in FIG. 4). With the addition of dTDP-L-olivose and dTDP-D-desosamine by sugar transferases, 8,8-α-deoxyoleandolide production increased biosynthesis of oleandomycin. By adding appropriate sugar transferase and sugar synthesizing genes, the production of oleandomycin is greatly increased due to excess CoA produced through the engineered PanK pathway.

As an additional demonstration of increased production of secondary metabolites that rely on CoA or A-CoA, we studied the effect of increased intracellular CoA on narbonolide, as shown in FIG. 5. In FIG. 5, dTDP-D-desosamine levels were increased by increasing the appropriate glycosyltransferase enzymes DesVII and DesVIII (1). This leads to increased biosynthesis of polyketide compounds narbomycin (FIG. 5.) and pikromycin (not shown).

The polyketide biosynthesis pathway starting from coenzyme A (CoA) is shown in FIG. 6. Our results clearly demonstrate that overexpression of PanK enzyme and pantothenic acid supplementation in *Streptomyces* promotes intracellular CoA biosynthesis, which then leads to the overproduction of acetyl-CoA, propionyl-CoA, malonyl-CoA, and methylmalonyl-CoA—the essential starting units for the biosynthesis of polyketides. Further, the increased intracellular level of CoA was found to promote overproduction of polyketides.

This concept can be applied to the all the polyketides whose synthesis begins with CoA precursors. More examples of CoA compounds involving in polyketide biosynthesis are illustrated in the polyketides biosynthesis pathways in FIGS. 7 and 8. Thus, using the techniques illustrated here, it will be possible to increase the production of many different useful natural polyketides. Further, it is possible to produce novel polyketides in bacteria by engineering a modular polyketide synthase, because the enzymes are made of several subunits that can be mixed and matched in various combinations to produce novel enzymes and thus novel polyketides (2).

Work is underway to expand the concept described herein to increase the production of various polyketides as illustrated in FIG. 6-8. Further, we will also expand the concept to include other *Actinomyctes* species, such as *Streptomyces peucetius*. Further, in the future, we will obtain and apply our methodology to bacterial strains that have already been selected for high production of a particular polyketide, this further maximizing production.

All references are listed herein for the convenience of the reader. Each is incorporated by reference in its entirety.

1. Hong, et al. New olivosyl derivatives of methymycin/pikromycin from an engineered strain of *Streptomyces venezuelae*. FEMS Microbiol. Let. Vol. 238:391 (2004)
2. Pfeifer B. A., et al., Biosynthesis of Complex Polyketides in a Metabolically Engineered Strain of *E. coli*, Science 291:1790-2 (2001) ("The engineering potential of modular [polyketide synthase] is hampered by the limited capabilities for molecular biological manipulation of organisms (principally *Actinomycetes*) in which complex polyketides have thus far been produced.")
3. Thuy M L, et al., Expression of 2-deoxy-scyllo-inosose synthase (kanA) from kanamycin gene cluster in *Streptomyces lividans*, Biotechnol. Left. 27:465-70 (2005) (describing pIBR25 vector)
4. Vadlai R. V. et al., Cofactor Engineering of Intracelluar CoA/acetyl-CoA and its Effect on Metabiolic Flux redistribution in *E. coli*, Metab. Eng. 6:133-139 (2004) (describing the engineering of *E. coli* to increase CoA compounds).

What is claimed is:

1. An engineered *Actinomycetes* cell comprising an overexpression of a recombinant pantothenate kinase (panK) gene wherein the overexpression of said recombinant panK gene increases pantothenate kinase activity and polyketide synthesis and increases acetyl-coA levels 2 fold greater than in *Actinomycete* cells without said overexpressed panK gene.

2. The engineered *Actinomycetes* cell of claim 1, wherein said panK gene is expressed from a chromosomal integration.

3. The engineered *Actinomycetes* cell of claim 1, comprising a panK gene from Table 2.

4. The engineered *Actinomycetes* cell of claim 3, comprising an *E. coli* panK gene.

5. The engineered *Actinomycetes* cell of claim 1, further comprising a recombinant DNA encoding a sugar transferase, glycosyltransferase, sugar synthase, glycosylsynthase, sugar dehydratase, and combinations thereof.

6. The engineered *Actinomycetes* cell of claim 5, wherein said recombinant DNA encodes a protein selected from the group consisting of DesVII, DesVIII, elloramycin glycosyltransferase (ElmGT), dNDPD-hexose synthase dNDPD-hexose-4,6-dehydratase, and combinations thereof.

7. A method of making polyketide comprising: growing the engineered *Actinomycetes* cell of claim 1 in a culture medium supplemented with pantothenic acid so as to produce more polyketide than a wild type *Actinomycetes*.

8. A method of increasing polyketide production in an *Actinomycetes* cell comprising:
  a) producing an engineered *Actinomycete* cell that overexpresses a recombinant pantothenate kinase (panK) gene,
  b) selecting an engineered *Actinomycete* cell that has chromosomal integration of said recombinant panK gene; and c) growing said engineered and selected *Actinomycete* cell in a medium supplemented with pantothenic acid, wherein said engineered and selected *Actinomycete* cell produces more polyketide than a wild type *Actinomycete* grown in said medium and wherein acetyl-coA is increased 2 fold greater than in *Actinomycete* cells without said overexpressed panK gene.

9. The method of claim 8, wherein the *Actinomycete* is *Streptomyces*.

10. The method of claim 9, wherein the *Actinomycete* is *Streptomyces venezuelae* or *Streptomyces peucetius*.

11. The method of claim 8, wherein said panK gene is selected from table 2.

12. The method of claim 11, wherein said panK gene an *E. coli* panK gene.

13. A method of increasing polyketide production in an *Actinomycetes* bacteria comprising:
   a) transforming an *Actinomycete* bacteria with a vector that encodes a pantothenate kinase (panK) gene,
   b) selecting a transformed *Actinomycete* bacteria that has chromosomal integration of said panK gene; and
   c) growing said transformed and selected *Actinomycete* bacteria under conditions that allow overexpression of said panK gene and in a medium supplemented with pantothenic acid, wherein said transformed *Actinomycete* bacteria produces more polyketide than a non-transformed *Actinomycete* bacteria grown in said medium and wherein acetyl-coA is increased 2 fold greater than in *Actinomycete* cells without the panK gene.

14. The method of claim 13, wherein the *Actinomycete* is *Streptomyces*.

15. The method of claim 14, wherein the *Actinomycete* is *Streptomyces venezuelae* or *Streptomyces peucetius*.

16. The method of claim 13, wherein said panK gene is selected from table 2.

17. The method of claim 16, wherein said panK gene is an *E. coli* panK gene.

* * * * *